(12) United States Patent
Schermeier et al.

(10) Patent No.: US 11,380,437 B2
(45) Date of Patent: Jul. 5, 2022

(54) SELECTION OF A MEDICAL ACCESSORY

(71) Applicant: FRESENIUS MEDICAL CARE DEUTSCHLAND GMBH, Bad Homburg (DE)

(72) Inventors: Olaf Schermeier, Frankfurt (DE); Kirill Koulechov, Bad Vilbel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 427 days.

(21) Appl. No.: 16/480,687

(22) PCT Filed: Jan. 29, 2018

(86) PCT No.: PCT/EP2018/052122
§ 371 (c)(1),
(2) Date: Jul. 25, 2019

(87) PCT Pub. No.: WO2018/138331
PCT Pub. Date: Aug. 2, 2018

(65) Prior Publication Data
US 2019/0392949 A1    Dec. 26, 2019

(30) Foreign Application Priority Data
Jan. 30, 2017  (DE) ..................... 10 2017 201 452.0

(51) Int. Cl.
*G16H 40/60* (2018.01)
*G16H 40/20* (2018.01)
(Continued)

(52) U.S. Cl.
CPC ............. *G16H 40/60* (2018.01); *G16H 10/60* (2018.01); *G16H 40/20* (2018.01); *A61B 34/25* (2016.02); *G16H 40/40* (2018.01)

(58) Field of Classification Search
None
See application file for complete search history.

(56) References Cited

U.S. PATENT DOCUMENTS

| 4,926,885 A | 5/1990 | Hinkle |
| 5,848,593 A | 12/1998 | McGrady et al. |

(Continued)

FOREIGN PATENT DOCUMENTS

| CN | 105373911 A * | 3/2016 |
| WO | 2008051460 A2 | 5/2008 |

OTHER PUBLICATIONS

Kuiper, Seth Alan; McCreadie, Scott R; Mitchell, John F; Stevenson, James G. "Medication errors in inpatient pharmacy operations and technologies for improvement." American Journal of Health-System Pharmacy 64.9: 955(5). American Society of Health-System Pharmacists. (May 1, 2007) . (Year: 2007).*

(Continued)

*Primary Examiner* — Linh Giang Le
(74) *Attorney, Agent, or Firm* — Kilyk & Bowersox, P.L.L.C.

(57) ABSTRACT

The invention relates to a method and an apparatus for selecting a medical accessory for treatment of a patient. The method comprises at least one of the following method steps. A first method step of receiving a patient identifier identifying the patient to be treated. A second method step of determining a treatment identifier of the treatment to be performed which identifies the treatment to be performed on the patient. A third method step of comparing an accessory database containing data sets on at least two medical accessories for one or more patient treatments to an actual inventory of stocked medical accessories. A fourth method step of selecting a suitable medical accessory for a treatment to be performed on the patient by means of the accessory database and on the basis of at least the patient identifier, the (Continued)

Figure 1:
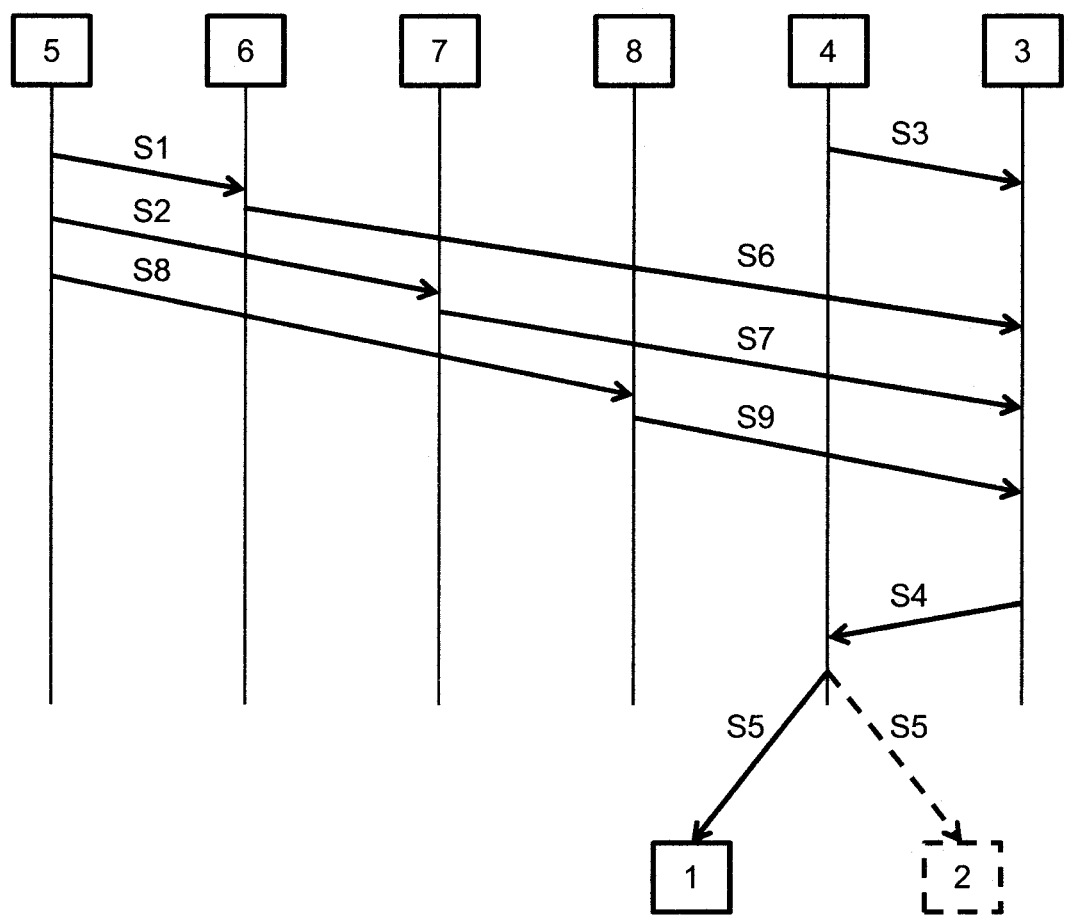

treatment identifier and the actual inventory. A fifth method step of segregating the selected medical accessory.

16 Claims, 6 Drawing Sheets

(51) Int. Cl.
  *G16H 10/60* (2018.01)
  *A61B 34/00* (2016.01)
  *G16H 40/40* (2018.01)

(56) References Cited

U.S. PATENT DOCUMENTS 7,685,026 B1 * 3/2010 McGrady ............... G07F 9/002
  705/28
2008/0185314 A1  8/2008 Tomasello et al.

OTHER PUBLICATIONS

International Preliminary Report on Patentability issued in corresponding International Patent Application No. PCT/EP2018/052122 dated Aug. 8, 2019 (7 pages).
International Search Report and Written Opinion issued in corresponding International Patent Application No. PCT/EP2018/052122 (with English translation of International Search Report) May 4, 2018 (13 pages).

* cited by examiner

SELECTION OF A MEDICAL ACCESSORY

This application is a National Stage Application of PCT/EP2018/052122, filed Jan. 29, 2018, which claims priority to German Patent Application No. 10 2017 201 452.0, filed Jan. 30, 2017.

The present invention relates to the field of medical technology and in particular to a technological method for selecting a medical accessory as well as a segregating apparatus and an apparatus for selecting medical accessories.

In the course of, particularly medically, treating a patient, in addition to the actual treatment itself, it is usually necessary to also provide the medical accessories the respective treatment requires. On the one hand, advances in medicine have yielded greatly diverse treatments with the accessories required becoming more numerous, diversified and specialized, which can result in rising expenditures in providing medical accessories to treat a patient. On the other hand, there is also the increasing desire in the medical sector, in particular with respect to the technological medical accessory logistics which come into play for the actual medical treatment, to provide for optimization and efficient use of resources coupled with a consistently high or even further increased quality of treatment.

The invention is based on the task of improving the provisioning of medical accessories, the selection of suitable medical accessories and/or efficient use of medical accessories to increase treatment safety and/or quality and/or lower the workload for individuals involved in the treatment of a patient.

The invention respectively solves this task by a method for selecting a medical accessory in accordance with the teaching of independent claim 1, a segregating apparatus for medical accessories according to the teaching of independent claim 14 and an apparatus for selecting a medical accessory according to the teaching of independent claim 15. Preferential embodiments, further developments or variants in particular constitute the subject matter of the independent claims. The subject matter of the claims is expressly made a part of the specification disclosure.

A first aspect of the invention relates to a method for selecting a medical accessory for a patient treatment. The method comprises at least the following method steps. In a first method step, a patient identifier which identifies the patient to be treated is received. In a second method step, a treatment identifier of the treatment to be performed identifying the treatment to be performed on the patient is determined. In a third method step, an accessory database, containing data sets on at least two medical accessories for one or more patient treatments, is compared to an actual inventory of stocked medical accessories. In a fourth method step, a suitable medical accessory is selected for a treatment to be performed on the patient by means of the accessory database and on the basis of at least the patient identifier, the treatment identifier and the actual inventory. In a fifth method step, the selected medical accessory is segregated.

In the sense of the invention, a "medical accessory" is a device, an instrument, a material, a substance or a combination thereof which is predetermined and/or applicable to the treatment of a patient. In particular, a medical accessory can be consumed in intended use. Alternatively, a medical accessory is not consumed in intended use; i.e. is used in multiple treatments of one or more patients. In particular, a medical accessory can be a medicinal product usually having at least substantially pharmacological, metabolic or immunological effect in intended use. Preferentially, such a medicinal product is of a pharmaceutical form, preferably for instance capsules, pills, tablets, pastes, ointments, injection doses or drug solutions, of a predetermined dosage, with a dosing device, administering device and/or storage device for the treatment, preferably for instance capsules or tablets in a blister pack, syringes with single or multiple doses of a injectable drug, medical syrups in bottles with or without dosage measuring cups or pharmaceutical preparations in a spray bottle having a spraying system. In particular, a medical accessory can be also a medicinal product usually having at least substantially somatic, physical or physicochemical effect in intended use or by means of which a pharmaceutical is administered. Such medicinal products are in particular surgical instruments such as surgical hooks, retractors, spreaders, scalpels, scissors or forceps. Such medicinal products are in particular also needles, syringes, cannulas, Seldinger wires or catheters. Protective gear for patients or individuals participating in the treatment can also be a medical accessory in the sense of the invention. Such protective gear in particular includes gloves to protect against chemicals or infection, preferably disposable gloves for instance made of latex, nitrite rubber or vinyl, medical mouthguards, medical hair nets or protective glasses. In particular, disinfectants, dressing materials or cosmetic products can also be medical accessories in the sense of the invention.

A medical accessory in the sense of the invention constitutes in particular a device, an instrument, a material, a substance or a combination thereof for patient cannulation. This in particular includes syringes, cannulas, infusion tubes, disposable gloves, disinfectants, swabs, dressing material, bandages, tapes and adhesive strips.

In addition, a medical accessory in the sense of the invention has physical dimensions and a weight which enables an individual participating in the treatment to transport and/or handle the medical accessory. Thus, the weight of such a medical accessory is in particular no more than 10 kg, preferably no more than 1 kg, preferably no more than 300 g, preferably no more than 100 g and further preferentially at the most 30 g. The physical dimensions to such a medical accessory are in particular of a length of no more than 1.5 m, preferably no more than 1 m, preferably no more than 0.5 m, preferably no more than 30 cm, preferably no more than 15 cm and further preferentially at the most 5 cm, wherein the same applies to the width and height. It is thereby needless to say that particularly the physical dimensions of such a medical accessory, such as an infusion tube or a tape, can also vary upon being unrolled, rolled or sectioned, whereby relevant to the handling or transport is that the physical dimensions of such a medical accessory is variable to the extent of exhibiting no more than the length, width and depth indicated above.

Preferably, the medical accessory in the sense of the invention can be designed and in particular configured such that a treatment apparatus for treating a patient can utilize the medical accessory in the treatment; in particular accommodate, operate, manipulate and/or administer.

"Treatment of a patient" in the sense of the invention refers to at least one medical; i.e. in particular therapeutic, diagnostic or cosmetic, procedure which effects changes to the body and/or health of the patient or by means of which the state of the patient's health is determined. A treatment is in particular an administration of medicinal products, a cannulation, a blood purification procedure such as dialysis, an operation and/or an examination of the patient.

As defined by the invention, the "segregating" of an object, in particular a medical accessory or accessory set, is the physical or logical segregating of the object. In particular, in physical segregating, the object to be segregated is physically separated from the other objects and preferably transported to a specific spatial area. Preferably, in physical segregating, the object to be segregating can be transported to a releasing or dispensing area, for instance an output location—in particular transported to a segregating apparatus—and provided there for the physical output, releasing or dispensing and/or physically output, released or dispensed respectively. In logical segregating, the object to be segregated can in particular remain in the spatial area in which it is already situated, whereby the object to be segregated is separated and/or distinguished from the other objects by means of designating and/or identifying the object to be segregated, preferably in a database or by means of an allocation rule for objects to be segregated and/or by applying a physical marking to or along with the object to be segregated.

A "patient identifier" in the sense of the invention is an identification which identifies a specific patient or a specific group of patients. In particular, the specific patient or specific patient group to which a specific patient is assigned can be identified by means of the patient identifier. A patient identifier is in particular a patient number, a patient name, provided it is explicit or can be made explicit by an additional identifier, a (health) insurance number, an ID number or unique number/name of the specific patient group. A respective group of patients in the sense of the invention can in particular be male or female patients, patients with a specific chronic illness, patients having a certain blood type, patients having a certain skin type, dialysis patients with arteriovenous fistula (AV fistula)—i.e. with a Cimino shunt, dialysis patients with vascular graft access (AV graft)—i.e. in particular with a Scribner shunt—or dialysis patients who require a central venous catheter line.

A "treatment identifier" in the sense of the invention is an identification which identifies a specific treatment or a specific group of treatments. In particular, the specific treatment or specific treatment group to which a specific treatment is assigned can be identified by means of the treatment identifier. A treatment identifier is in particular a treatment number or a unique designation for a treatment or a group of treatments. A respective group of treatments in the sense of the invention can be specific operations, a specific illness therapy, initial patient examinations or dialysis treatments, which in turn can comprise subgroups, in particular hemodialysis, hemofiltration, hemodiafiltration, hemoperfusion or peritoneal dialysis treatments.

The method according to the invention for selecting the medical accessory, enables selecting a medical accessory which is suited to the treatment to be performed as well as the patient, and also in stock, from the medical accessories based on data sets within the accessory database. In particular, the selection process can be automated and/or the selected medical accessory segregated automatically. The provision of medical accessories can thereby advantageously be improved and in particular personnel freed up compared to conventional medical accessory logistics. One advantage of at least the method enabling a structured and preferably automated selection also lies in being able to reduce sources of error, in particular human failure, with treatment safety thus being able to be increased. A further advantage can be, particularly with a plurality of medical accessories, patients and/or treatments, being able to select a particularly applicable medical accessory by means of the accessory database, with the quality of the treatment thus being able to be increased. In the process, a medical accessory can for instance be selected for the same treatment to be performed on one patient which is particularly suited to said patient while a different medical accessory is selected for another patient which is particularly suited to that patient. In particular, a specific type of cannula can thereby be particularly suited for cannulation of the one patient while a different type of cannula in cannulation—and e.g. subsequent dialysis—provides better treatment results for the other patient and is thus better or respectively particularly suitable for the other patient. Moreover, selection from a plurality of suitable medical accessories by means of the accessory database enables prioritized use of an accessory, and consumption as applicable, in terms of acquisition costs, storage costs and/or expiration date, whereby an efficient use of resources, i.e. in particular the stocked and/or to be procured medical accessory, can be achieved. Lastly, the segregating of the selected medical accessory enables, especially compared to a conventional—in particular unselected or undefined/non-specifically selected—provision of medical accessories, the respectively applicable medical accessory to be provided for the treatment; i.e. in particular only the suitable medical accessory and not unsuited medical accessories. This thereby advantageously prevents or at least reduces the use of unsuitable medical accessories, whereby the treatment quality and/or treatment safety can be increased. In particular in the case of a patient who has a specific intolerance or allergy, this prevents a pharmaceutical, disinfectant or medicinal product to which the patient has an intolerance, such as latex gloves in the case of a latex allergy, from even being made available at all and thereby being able to instead use another suitable available accessory such as a nitrile rubber glove in the case of latex allergy.

According to a first preferential embodiment, the method further comprises the following method steps. In one further method step, one or more patient characteristics is/are determined by means of the patient identifier based on an allocation rule for patient characteristics constructed to allocate one or more patient characteristics to a respective patient identifier. In a further method step, one or more treatment characteristics are determined by means of the treatment identifier and by means of an allocation rule for treatment characteristics which allocates one or more predetermined treatment characteristics of the respective treatment in each case to at least two treatments. In this preferential embodiment, at least two data sets of the accessory database in each case identify one or more characteristics from the group of accessory characteristics, patient characteristics and treatment characteristics. In addition, to select the suitable medical accessory by means of the accessory database, a medical accessory is identified, its associated data set exhibiting accessory characteristics, patient characteristics and/or treatment characteristics which correspond to the specific patient characteristics determined on the basis of the patient identifier or the specific treatment characteristics determined on the basis the treatment identifier respectively.

As defined by the invention, "constructed" refers at least to the respective apparatus being predefined or definable—i.e. configurable—to perform a certain function. The configuration can thereby in particular ensue by means of appropriately setting process sequence parameters or by switches or the like for activating functionalities and/or settings. The configuration can thereby in particular also ensue by means of an appropriate arrangement, implementation or combination of one or more component parts of the respective apparatus.

A "patient characteristic" in the sense of the invention is a characteristic of a patient or a group of patients. Preferably, such a characteristic relates to a property of the patient or patient group which corresponds to an illness of the patient, a treatment to be selected to the patient, the health of the patient or the body of the patient. A patient characteristic is in particular the gender of the patient, a current or planned pregnancy, the presence of an AV fistula or an AV graft, the presence of a specific, in particular chronic, illness or affliction, the presence of an allergy or pharmaceutical intolerance, the skin type, the body height, the body weight, the arm circumference, the leg circumference, the age, one or more treatments already performed, still to be performed or to be concurrently performed, a genetic trait, or the medication of a specific pharmaceutical product.

A "treatment characteristic" in the sense of the invention is a characteristic of a treatment or a group of treatments. Preferably, such a characteristic relates to a property of the treatment or group of treatments which corresponds to an illness to be treated by way of the treatment, the method of treatment or individual procedural steps, one or more medical accessories required to carry out the treatment, a region of the body on which at least one part of the treatment is to be performed, the hygienic requirements during the treatment, treatment risks and/or complications or required safety precautions. A treatment characteristic is in particular the required access to a—in particular specific—blood vessel, a specific illness to be treated, specific medical accessory required for the treatment, an indicated patient pre-treatment or post-treatment—in particular prophylaxis or emergency procedures upon complications, the expected treatment duration, the possibility of pain occurrence during treatment, or parameters to be monitored, in particular vital parameters or vital functions, prior to, during or subsequent treatment.

An "accessory characteristic" in the sense of the invention is a characteristic of a medical accessory or a group of accessories. Preferably, such a characteristic relates to a property of the accessory corresponding to its storage requirements, risks and/or the necessary knowledge involved in using the accessory and/or its suitability for a specific treatment or a specific patient. Accessory characteristics can be in particular the weight of the accessory, its physical dimensions, price, expiration date, required storage conditions, the type or class of the accessory, the number of such accessory items actually in stock in the inventory, the color, or the dosage, quantity, size or area of such an accessory.

In particular, the patient characteristics or the treatment characteristics can correspond to the respective characteristics in the accessory database. In particular, a characteristic in a data set relative to a specific medical accessory can hereby correspond to a specific patient characteristic or treatment characteristic. Hence, the area of a cut-to-size bandage—thus an accessory characteristic—can correspond to the weight or the arm circumference of a patient—thus a patient characteristic—i.e. in particular a specific cut-to-size bandage being able to be particularly suited to a specific region of the arm circumference. Also the ability of a disinfectant to kill specific germs—thus an accessory characteristic—can correspond to the hygienic requirements for a specific treatment—thus a treatment characteristic—i.e. in particular a specific disinfectant being able to be particularly suited to a specific treatment having high hygienic requirements since it can in particular kill many germs or kill germs particularly reliably, whereas a different disinfectant, due for instance to its skin tolerability—thus a patient characteristic—is better suited to other treatments having lower hygienic requirements.

One advantage of selecting the suitable medical accessory via correspondence of characteristics can in particular be a medical accessory being able to indirectly correspond to multiple patients or treatments, and in particular without direct allocation, whereby the accessory database can be efficiently administered and/or the accessory database-based selection can be dynamically and/or flexibly adapted to new patients, treatments and/or medical accessories. New medical accessories or medical accessories having a data set expanded by the respective characteristics can thereby advantageously also correspond to existing patients or treatments and be selected for a patient and/or a treatment without additionally changing the allocation rule for patient characteristics or the allocation rule for treatment characteristics respectively. Accordingly, particularly a new patient can also correspond to existing treatments and/or medical accessories or, respectively, a new treatment can correspond to existing patients and/or medical accessories. Selecting a suitable medical accessory by way of characteristics correspondence additionally achieves multiple medical accessories corresponding to specific patient characteristics and/or treatment characteristics, thereby enabling an alternative selection from the multiple applicable accessories for a specific treatment and/or a specific patient. In addition, a specific medical accessory can also be directly allocated to a specific patient and/or a specific treatment, preferably by the accessory characteristics of the specific medical accessory comprising the patient identifier of the specific patient and/or the treatment identifier of the specific treatment or, respectively, by the patient characteristics of the specific patient comprising the specific medical accessory or an accessory identifier allocated to the medical accessory.

A further preferential embodiment moreover comprises the following method steps. One or more patient characteristics of the patient is received in a further method step from a patient examining device or a data network for patient characteristics. The received patient characteristic(s) is/are thereupon stored in a patient characteristic memory, by means of which the allocation rule for patient characteristics allocates one or more patient characteristics in each case to a patient identifier.

As defined by the invention, a "patient examining device" refers at least to an apparatus by means of which patient characteristics of a patient can be determined. In particular, an examining device can be designed to determine the patient's weight, specific physical dimensions—for instance height, arm circumference or leg circumference, skin type, blood properties, the arrangement or shape of blood vessels or a specific blood vessel, the colonization of a physical region with specific organisms—for instance the colonization of a specific region of the skin with Multi-Resistant Staphylococcus Aureus (MRSA)—or specific vital signs—for instance blood pressure, pulse, blood oxygenation, blood glucose level, respiration or body temperature.

A "patient characteristic memory" is an apparatus for storing and retrieving patient characteristics. Preferably, a patient characteristic memory is an electronic storage device which can in particular be a component part of a data processing device. A patient characteristic memory can hereby in particular be a memory area allocated in static or dynamic manner by an electronic storage device of a data processing device.

This advantageously enables using the patient characteristics from the examining device or the data network in the selecting of medical accessories.

According to a further preferential embodiment, a request signal for patient characteristics is sent to the patient examining device or the patient characteristics data network. This enables the receipt of patient characteristics to be automated, whereby sources of error can be reduced and/or the efficiency in selecting and/or providing medical accessories can be increased.

In a further preferential embodiment, the examining device determines one or more patient characteristics of the patient and sends them for receipt of patient characteristics in particular to the patient characteristics memory, the data network for patient characteristics and/or an apparatus for selecting medical accessories. This thereby advantageously enables the examining device to determine one or more patient characteristics, in particular automatically and prior to the selecting of a suitable medical accessory for the patient treatment to be performed, whereby particularly the quality, safety and/or efficiency of the treatment can be increased.

A further preferential embodiment further comprises the following method step. One or more patient treatments to be performed on the basis of the patient characteristics is determined in a further method step. This thereby advantageously enables the patient characteristics to not only be used for the selecting of medical accessories but also for determining one or more treatments to be performed. In particular, required or patient-advantageous pre-treatments or post-treatments can in this way be determined. This thereby also advantageously particularly enables ensuring that a treatment which is particularly suitable for the patient is determined or, vice versa, that another treatment, which is unsuitable, due for instance to a pharmaceutical intolerance or a chronic patient illness, is not determined as the treatment to be performed. In addition, a potential need for one or more medical accessories required for specific medical treatments can be predictively determined, whereby the risk of such medical accessories not being stocked can be lowered.

In a further method step of a further preferential embodiment, the treatments to be performed as determined on the basis of the patient characteristics are output to a user interface. In particular, it is possible for a user, in particular for an individual involved in the treatment, to note the treatments to be performed as determined on the basis of the patient characteristics and/or compare them to treatments to be performed determined in another manner. This thereby advantageously enables increasing the quality and/or safety of the treatment.

A further preferential embodiment comprises the further following method step to determine the treatment identifier of the treatment to be performed. A treatment which is to be performed first is selected in a further method step from among the patient treatments to be performed on the basis of a predefined criterion for treatment priority. In an even further method step, the treatment identifier of this treatment to be performed first is specified as the treatment identifier of the treatment to be performed. This thereby advantageously enables automating the selection of the treatment to be performed and, thus, in particular the efficiency increased and/or personnel workload reduced. Moreover, a standard procedure can be achieved based on the predefined treatment priority criterion upon given specific patient characteristics, whereby in particular the quality and/or safety of the treatment can be increased in addition to the efficiency.

A further preferential embodiment further comprises the following method step for determining the treatment identifier of the treatment to be performed. A user interface receives an input of the treatment to be performed in a further method step. This input is thereupon allocated to the respective treatment identifier in an even further method step. In a preferential variant, at least two treatments determined on the basis of the patient characteristics are initially output at the user interface, an input option is thereby provided to select the treatment to be performed from the treatments as output, and ultimately the input of the treatment to be performed from the selected treatments is received. Particularly compared to an automated selecting of the treatment to be performed, a user, in particular an individual involved in the treatment, can specify the treatment to be performed by means of input, preferably freely or within a predefined preselection of possible treatments, whereby the treatment quality and/or treatment safety and/or efficiency can be increased based on the user's expertise—and with preselection, additionally on basis of the patient characteristics.

According to a further preferential embodiment, to select the suitable medical accessory, a first suitable accessory is determined by means of the accessory database and, if same is not available in the actual stock, ascertaining an alternative suitable accessory until determining said respective alternative suitable accessory is in stock or until it is determined that none of the suitable accessory alternatives are in stock. One advantage of this selection of the applicable accessory can in particular lie in the fact that provided a suitable medical accessory is in fact in the actual stock, same will also be ultimately selected. In particular, this enables the provisioning of medical accessories to be improved and also an appropriate medical accessory selection to be achieved when resources are scarce; i.e. when there is a shortage of specific types of medical accessories. Also, in one preferential variant, the most economical, as well as also stocked, medical accessory can respectively be selected from among suitable options, whereby medical accessory costs can be reduced.

In a further preferential embodiment, at least two data sets of the accessory database identify in each case the expiration date of the medical accessory associated with the respective data set. This embodiment further comprises one or more of the following method steps. A medical accessory is identified as not in stock in a further method step if same is past its expiration date. In an even further method step, a medical accessory which is past its expiration date is isolated. In an even further method step, a medical accessory disposal signal is output which in particular identifies the expired medical accessory to be isolated and/or discarded. This thereby advantageously enables ensuring that only unexpired medical accessories will be selected and/or that expired medical accessories will actually be removed from the inventory; in particular isolated, or that at least the necessary disposal be will signaled.

In a further preferential embodiment, at least two data sets of the accessory database identify in each case the required medical accessory storage conditions associated with the respective data set. This embodiment further comprises one or more of the following method steps. At least two storage areas are provided in a further method step, each with their own respective storage conditions, with the storage conditions preferably being able to be separately controlled or regulated. In an even further method step, a portion of the medical accessories is in each case stored in one of at least two storage areas in which the storage conditions at least substantially correspond to the required storage conditions of the respective medical accessories. The actual storage conditions prevailing for the actual inventory of stocked medical accessories is detected in a further method step. In an even further method step, a medical accessory is identified as not in stock when the actual storage conditions of the medical accessory differ and/or have deviated from the required storage conditions according to a criterion for medical accessory spoilage. In a further method step, a medical accessory with actual storage conditions which differ and/or have deviated from the required storage conditions according to a medical accessory spoilage criterion are isolated, in particular into a segregation area. In an even further method step, a medical accessory disposal signal is output which identifies the medical accessory with actual storage conditions having differed and/or deviated from the required storage conditions and which is in particular to be isolated and/or discarded. One advantage of storage conditions adapted to the respective medical accessory can be accessories not degrading during storage or at least no more than inevitable and/or not degrading prior to the expiration date. An advantage of the at least two storage areas can lie in medical accessories having different storage conditions requirements being able to be initially stored and thus available for the medical accessory selection. This thereby advantageously enables reducing the costs for medical accessories and their disposal, in particular due to expiration, and/or efficiently storing as well as providing of medical accessories subject to different storage conditions. It can also be ensured that only a medical accessory which adhered to its storage conditions will be selected and/or that a medical accessory which failed to adhere to its storage conditions will be removed from the actual inventory and/or at least its necessary disposal signaled. This thereby advantageously enables the quality and/or the safety of the treatment to be improved.

According to a further preferential embodiment, at least two medical accessories are assembled into a medical accessory set in predetermined manner. In addition, the accessory database comprises at least one data set on the medical accessory set and/or the data sets on the at least two medical accessories of the accessory set also identifies the medical accessory set in addition to the respective medical accessories. Moreover, the accessory database is compared to the actual inventory of stocked medical accessory sets. Lastly, the medical accessory set for the treatment to be performed on the patient is selected when one, at least two, or all of the medical accessories of the medical accessory set are selected for the treatment and the medical accessory set is segregated instead of the individual medical accessories.

As defined by the invention, a "medical accessory set" is an assemblage of at least two medical accessories. In particular, a medical accessory set can comprise an accommodating device, in particular a container, designed to accommodate the at least two medical accessories; i.e. in particular detachably connect to same in form-fit, force-fit or materially bonded manner and/or enclose same and/or wherein the at least two medical accessories are ordered in the accommodating device. In particular, such an accommodating device for medical accessories is an accessory box in the sense of the invention. Preferably, such an accessory box can comprise an assemblage of at least two medical accessories for a specific treatment. In particular, such an accessory box can be pre-equipped with a specific assemblage of medical accessories for a specific treatment. Also preferably, a medical accessory set or in particular an accessory box can comprise one or more retention devices for respectively accommodating medical accessories. In particular, medical accessories for a specific treatment can thereby be specifically arranged, preferably on the basis of their order of use in the specific treatment. Preferably, a medical accessory set and in particular a medical accessory box are configured and in particular formed such that a treatment apparatus for the treatment for which the accessory set is intended or an individual participating in the treatment can handle and/or utilize the accessories during the treatment; i.e. in particular hold, open, manipulate and/or remove medical accessories of the accessory set.

In particular, at least two medical accessories of which usually both are necessary for a specific treatment can thus be assembled into a medical accessory set. This thereby advantageously enables reducing the number of medical accessories to be selected and segregated for a specific treatment, whereby efficiency increases, there is less burden on personnel and/or safety is increased since all the medical accessories necessary for the treatment to be performed are actually available and present at the treatment location. In addition, the transport and/or use of the medical accessories for a treatment can be improved by compiling them into one or more accessory boxes.

A further preferential embodiment moreover further comprises the following method steps. In one further method step, a medical accessory set for the patient treatment to be performed is assembled based on the selection of one or more suitable medical accessories for the patient treatment to be performed. In a still further method step, the assembled medical accessory set is segregated instead of each applicable medical accessory individually and/or instead of at least some of the medical accessories applicable or respectively necessary for the treatment. One advantage of assembling the medical accessory set based on the medical accessories needed for the treatment to be performed can relate to all or at least some of the medical accessories needed for the treatment being able to be assembled as an accessory set and thus transported and/or handled collectively, whereby efficiency increases and/or the risk lowers of some medical accessories not being available or provided at the treatment location due for instance to the plurality of different medical accessories required for the treatment. A further advantage can relate to the accessory sets being able to be adapted to the respective treatment to be performed and it thus not being necessary to keep a large number of different pre-assembled accessory sets in stock. This thereby advantageously enables achieving flexible adapting to patient and/or treatment requirements. In one preferential variant, the medical accessories of the accessory set are arranged in an accessory box such that the respective medical accessories required for a treatment step of the treatment to be performed are adjacently arranged and/or a medical accessory required for a subsequent treatment step is arranged adjacent to a medical accessory required for the preceding treatment step. In particular, the arrangement of the medical accessories in this way advantageously corresponds to the order of the treatment steps, whereby the handling and in particular grasping of the respectively required medical accessories can be accelerated and/or facilitated and/or treatment safety increased.

A further preferential embodiment moreover further comprises the following method steps. In one further method step, a practitioner identifier is received which identifies an attending person or a treatment apparatus for the patient treatment to be performed. In a still further method step, one or more practitioner characteristics are determined on the basis of the practitioner identifier and by means of an allocation rule for practitioner characteristics configured to allocate one or more practitioner characteristics in each case to a practitioner identifier. In this preferential embodiment, at least two data sets of the accessory database identify in each case at least one of the practitioner characteristics and/or at least one of their accessory characteristics in correspondence with at least one of the practitioner characteristics. In addition, in the selecting of the suitable medical accessories by way of the accessory database, a medical accessory or accessory set is determined, its associated data set comprising practitioner characteristics or accessory characteristics which correspond to the practitioner characteristics determined on the basis of the practitioner identifier.

As defined by the invention, a "practitioner identifier" is an identifier which indicates a specific individual involved in the treatment or with a treatment apparatus for the treatment, or a group of such individuals and/or treatment apparatus. In particular, the specific individual or treatment apparatus or group of specific individuals and/or treatment apparatus can be identified by means of the practitioner identifier. A practitioner identifier is in particular a personnel number for individuals, an inventory number for treatment apparatus, a name of the attending person, provided it is explicit or can be made explicit by an additional identifier, an identification number or an explicit number or explicit name respectively of the specific group of people and/or treatment apparatus.

An individual involved in the treatment can in particular be an attending person, for instance a physician, or an individual providing treatment support, for instance a nurse. In particular, the patient to be treated can himself also be an individual involved in the treatment or an attending person.

As defined by the invention, a "treatment apparatus" is to at least be understood as an apparatus which is equipped to perform and/or support one or more patient treatments. A treatment apparatus is in particular a surgery robot, a cannulation apparatus, a dialysis apparatus or a disinfecting apparatus for disinfecting an area of a patient's body.

As defined by the invention, a "practitioner characteristic" is a characteristic of an individual involved in the treatment, a treatment apparatus or a group of involved individuals and/or treatment apparatus. Preferably, such a characteristic relates to a property of the individual, treatment apparatus or group which corresponds to the using and/or operating of at least one of the medical accessories required for the treatment. In the case of personnel, a practitioner characteristic can in particular be hand size, existing allergies or intolerances, in particular preferences and/or proficiencies for or with specific medical accessories, vision—e.g. wears corrective lenses—, body size or head circumference. In the case of treatment apparatus, a practitioner characteristic can in particular be a technical property of the treatment apparatus, preferably relating to whether the treatment apparatus is equipped to use a specific medical accessory or accessory set and/or perform a specific treatment.

One advantage of suitable medical accessories being at least partly selected via practitioner characteristics correspondence can be a medical accessory being able to indirectly correspond to multiple persons and/or treatment apparatus involved in the treatment and in particular without direct allocation, whereby the accessory database can be efficiently administered and/or the accessory database-based selection can be dynamically and/or flexibly adapted to a new medical accessory and/or persons/treatment apparatus participating in the treatment. In particular, the above-cited advantages and further developments related to selecting a suitable medical accessory by way of characteristics correspondence also applies to selection by way of practitioner characteristics correspondence. Preferably, this correspondence enables selecting and segregating disposable gloves for a treatment to be performed in the right size and/or of suitable material for an attending physician—for instance nitrile rubber gloves for those with latex allergies. Likewise preferably, in the case of a treatment apparatus, a medical accessory or accessory set can be selected which is able to be operated by said treatment apparatus, in particular automatically.

According to a further preferential embodiment, at least one of the, preferably all, method steps and preferably also the parameters of the respective method step are logged; i.e. in particular the method step performed and/or its parameters stored, preferably with an indication of time and/or location. This advantageously enables procedures to be reproduced at a later point in time, in case of failure if necessary, and/or increasing the treatment safety. A further advantage can lie in the need for medical accessories to date being determined as well as in particular a future need being able to be predicted on the basis of same. Medical accessories can thus be predictively ordered and/or a shortage of actual medical accessory inventory or the non-availability of a specific medical accessory prevented. In a further preferential variant, the actual storage conditions and/or deviations of the actual storage conditions from the required storage conditions are thereby logged at regular or intermittent time intervals and/or logged subject to occurrence of a condition—for instance, preferably a deviating of the actual storage conditions from the required storage conditions.

A further preferential embodiment moreover comprises the following method step: Selecting and segregating an additional medical accessory which is, identical or at least similar to the suitable medical accessory selected for the medical treatment. According to a preferential variant, this method step is only realized when the applicable medical accessory selected for the treatment is indicated in an additional accessories allocation rule identifying medical accessories, in particular as a function of the respective treatment to be performed, as becoming damaged prior to or upon being used during treatment or treatment preparation, in particular routinely or frequently—preferably in at least 10% of cases, preferably in at least 50% of cases and further preferentially in at least 8% of cases—without the respective treatment or respective treatment step being able to be performed; i.e. in particular requiring a replacement of the medical accessory. The additional medical accessories thereby advantageously provides a replacement. According to a further preferential variant, in which a medical accessory set is segregated, an additional similar medical accessory set is selected/assembled and segregated as a replacement. A further advantage of particularly this variant lies in the fact that as long as the treatment can be performed with the medical accessory set segregated in the regular procedure, the additional medical accessory set does not need to be used or opened and hence, in particular, not consumed and/or can be returned to the actual inventory again.

A second aspect of the invention relates to a segregating apparatus for medical accessories which is configured to segregate medical accessories or accessory sets selected in accordance with the first aspect of the invention.

The potential advantages as well as embodiments, further developments or variants of the first aspect of the invention already cited previously also apply accordingly to the segregating apparatus according to the invention.

A first preferential embodiment of the segregating apparatus comprises an identification device which is configured to identify an attending person, a treatment apparatus or a transporting person or transport apparatus associated with the attending person or treatment apparatus and determine an associated practitioner identifier. Furthermore, the preferential embodiment is designed to only segregate the medical accessory or accessory set when the associated practitioner identifier determined by the identification device corresponds to the practitioner identifier in the medical accessory selection according to the first aspect of the invention.

As defined by the invention, a "transporting person" is to be understood as an individual who transports at least medical accessories and/or accessory sets from a location where they are output, in particular by a segregating apparatus or by a selection apparatus, to a treatment location. In particular, an individual participating in the treatment can thereby also be a transporting person in the sense of the invention. A treatment location is in particular a site at which the respective treatment is to be performed and/or at which the medical accessories or accessory set need to be positioned in order to perform the respective treatment.

As defined by the invention, a "transport apparatus for medical accessories" is to be understood as an apparatus which is configured to transport at least medical accessories and/or accessory sets from a location where they are output, in particular by a sorting apparatus or by a selection apparatus, to a treatment location. A medical accessory transport apparatus is in particular a logistics robot or a pneumatic tube system.

This thereby advantageously enables increasing treatment safety and/or lessening the workload of personnel. In particular, the medical accessory transporting person or transport apparatus can in this way provide and/or segregate the respective medical accessory to be transported by said transporting person or transport apparatus.

A third aspect of the invention relates to a selection apparatus for a medical accessory or accessory set which is configured to realize a method in accordance with the first aspect of the invention and which comprises one or more segregating apparatus, in particular in accordance with the second aspect of the invention. Preferably, the selection apparatus comprises a computer program having a program code for implementing a method according to the first aspect of the invention. Further preferentially, the selection apparatus comprises a non-volatile electrical data storage, in particular at least one hard disk, read-only memory (ROM), or drive with a data medium which stores the computer program. Further preferentially, the selection apparatus comprises at least one data processing device for executing the computer program. It can thereby in particular comprise a microprocessor, a non-volatile electrical data storage as well as at least one data interface. Preferably, the data processing device also comprises a volatile electrical data storage, in particular as main memory, preferably a semiconductor memory, in particular with integrated capacitors and/or flip-flops (bistable multivibrators) for data storage, for instance dynamic RAM or static RAM.

The potential advantages as well as embodiments, further developments or variants of the first and/or second aspect of the invention already cited previously also apply accordingly to the inventive selection apparatus.

The present invention also explicitly relates to a system for medical accessories having a selection apparatus according to the third aspect of the invention and at least one treatment apparatus. Preferably, the system further comprises at least one transport apparatus.

The potential advantages as well as embodiments, further developments or variants already cited previously also apply accordingly to the inventive system.

Further advantages, features and possible applications of the present invention are yielded by the following detailed description of at least one preferential embodiment and/or by the figures. Unless otherwise described or contextually indicated otherwise, the same reference numerals are substantially used to identify equivalent components in the example embodiments.

Figure 2:
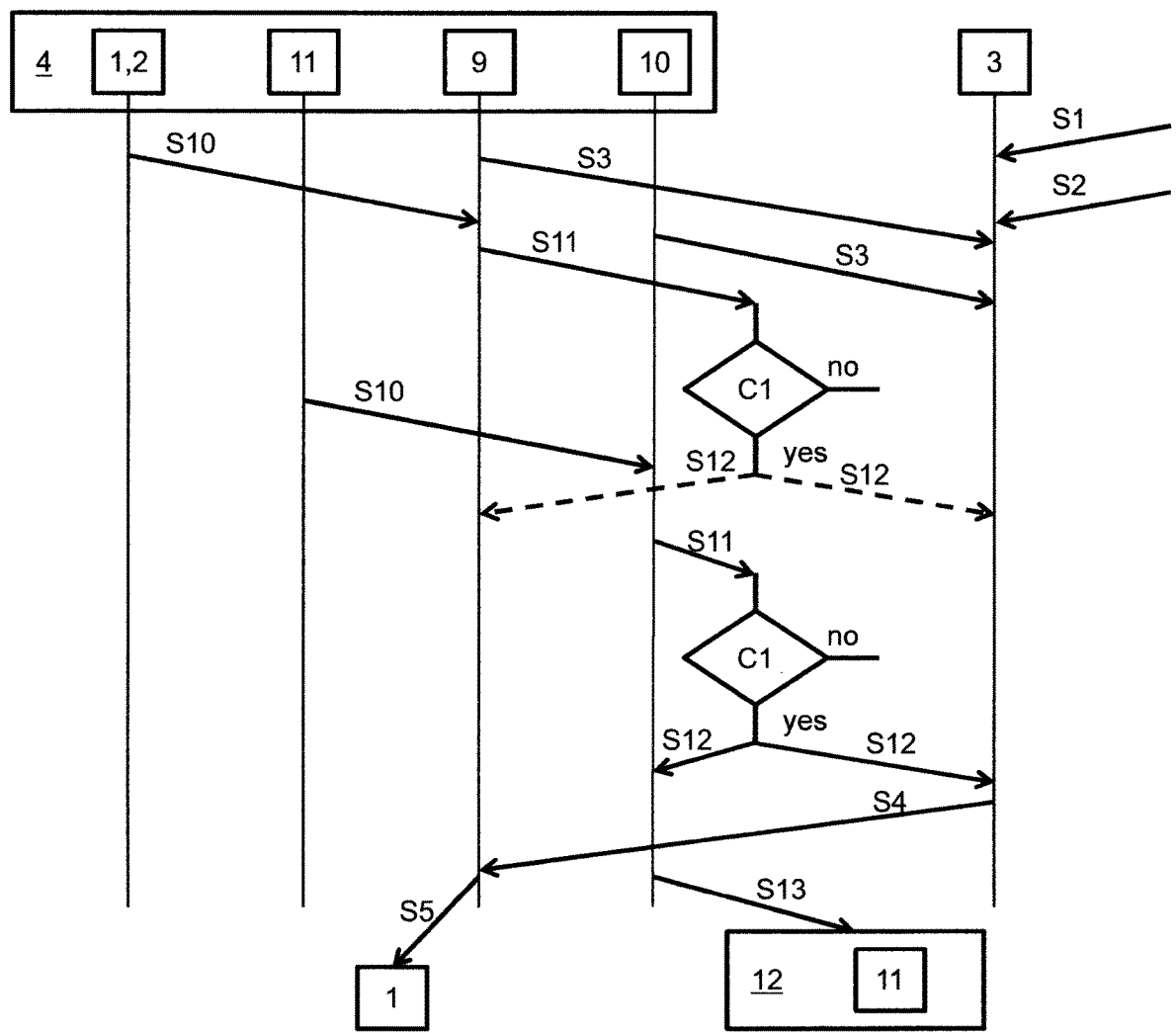
Figure 3:
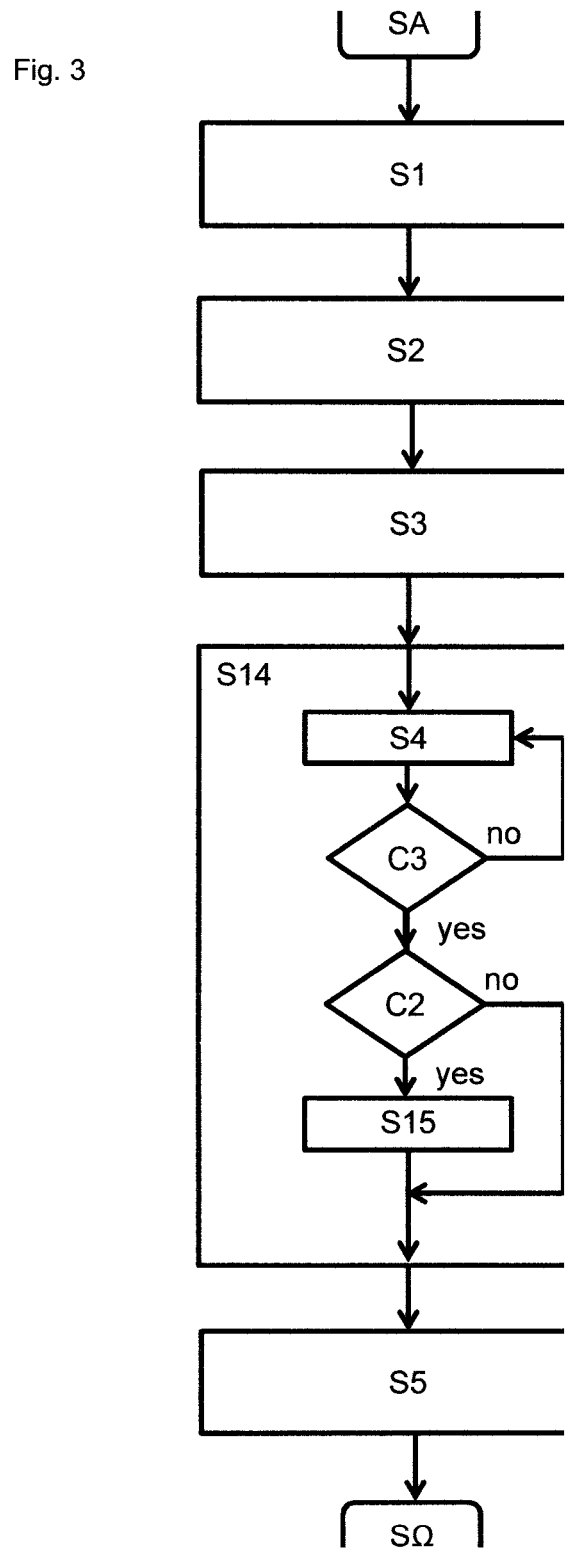
Figure 4:
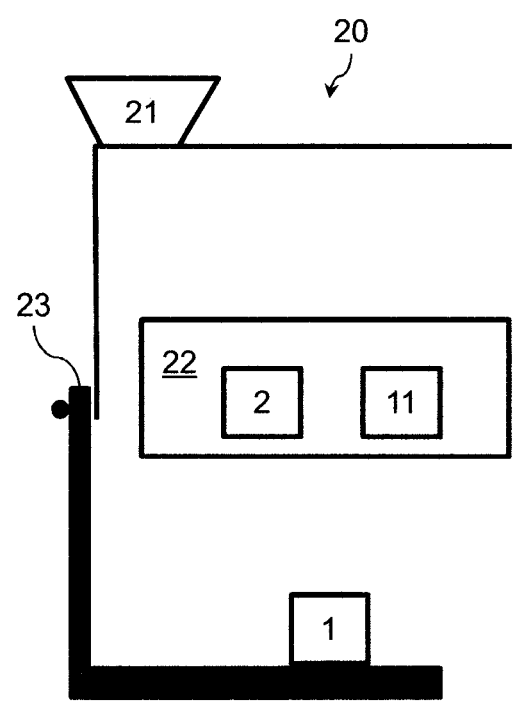
Figure 5:
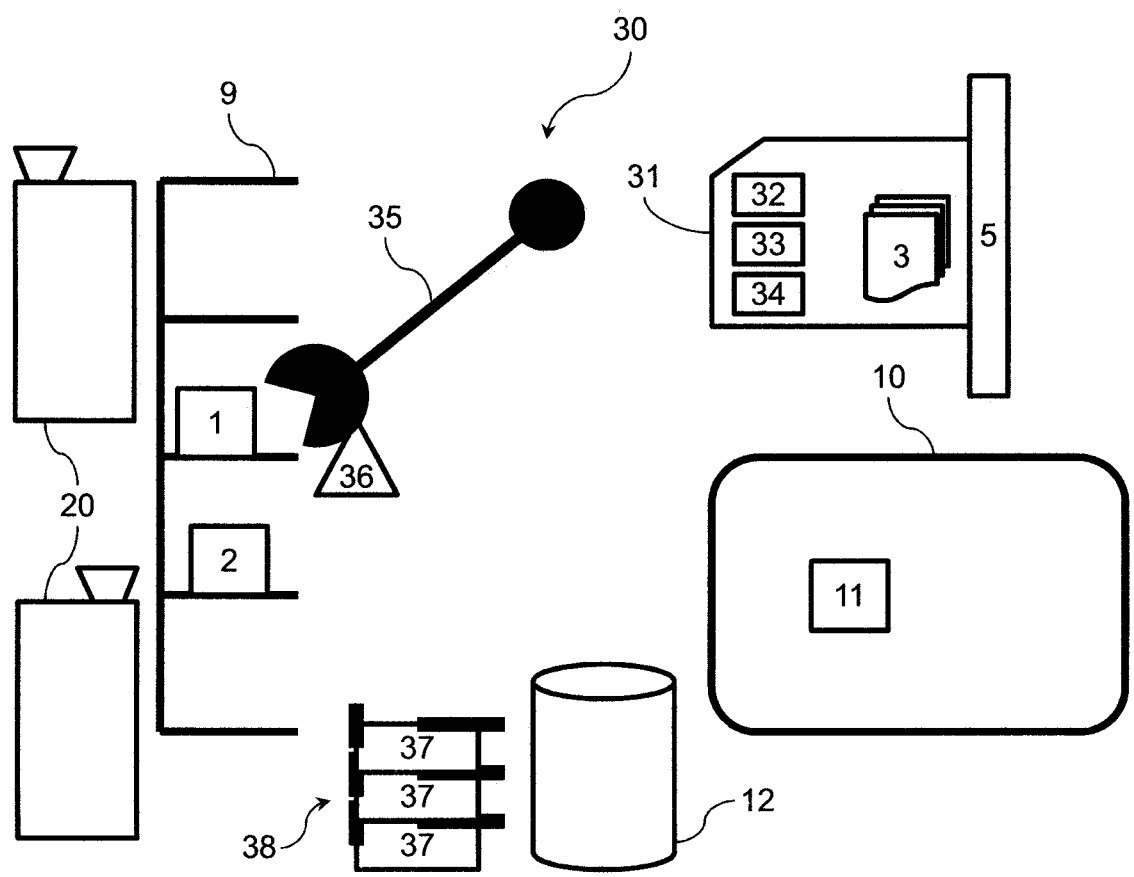
Figure 6:
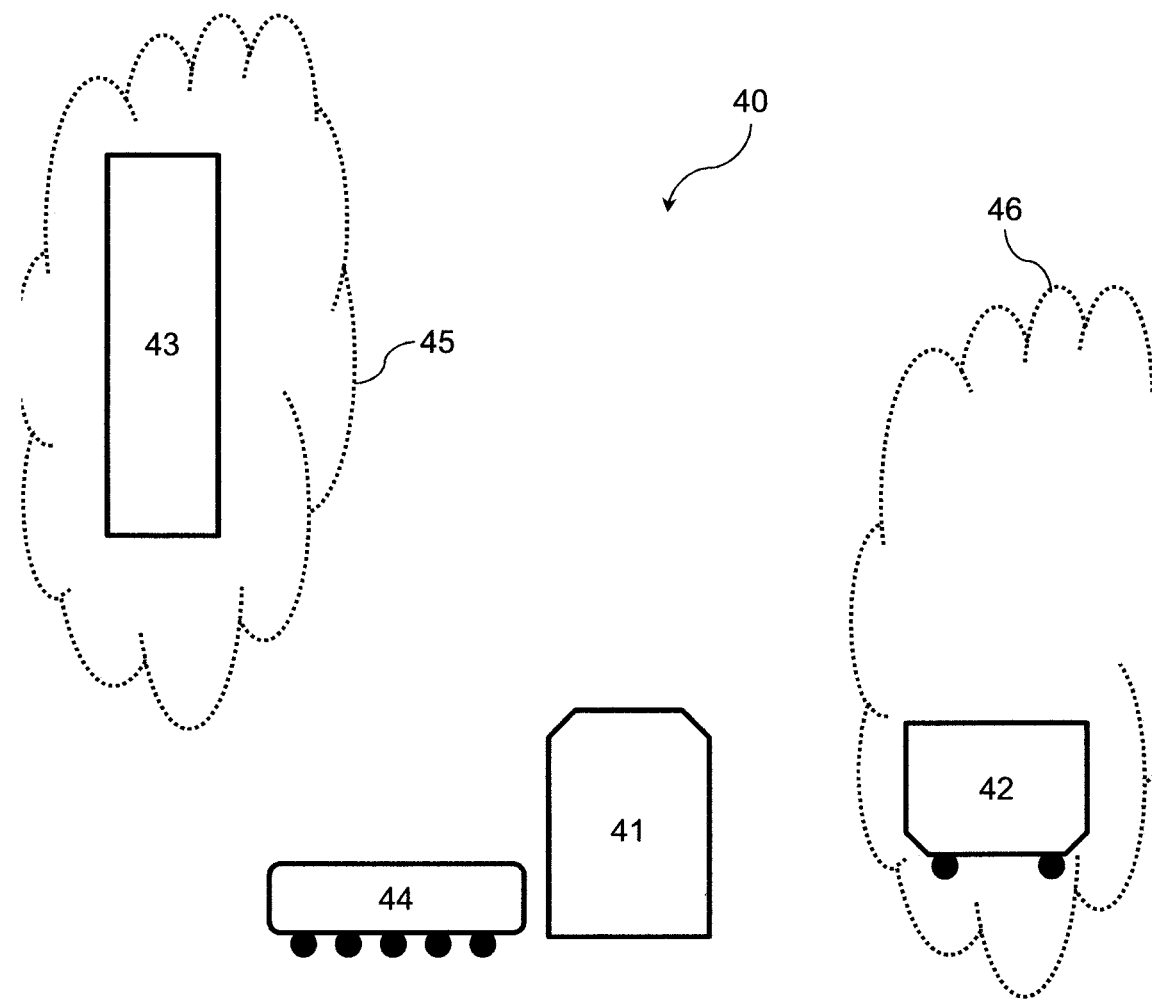

Thereby shown, to some extent schematically:

FIG. 1 a flow chart to illustrate a preferential embodiment of the inventive method for selecting a medical accessory;

FIG. 2 a flow chart to illustrate a further preferential embodiment of the inventive method for selecting a medical accessory;

FIG. 3 a flow chart to illustrate a still further preferential embodiment of the inventive method for selecting a medical accessory;

FIG. 4 an embodiment of the inventive segregating apparatus for medical accessories;

FIG. 5 an embodiment of the inventive selection apparatus for medical accessories; and FIG. 6 an embodiment of the inventive system for medical accessories.

FIG. 1 depicts a flow chart illustrating a preferential embodiment of the inventive method for selecting a medical accessory 1, 2. The medical accessory can hereby also be an accessory set 2 which is in particular designed as a container and comprises at least two medical accessories arranged in the container.

A patient, a treatment to be performed as well as an attending person and/or a treatment apparatus for the treatment is first input at a user interface 5, in particular as methods steps of the method according to the present preferential embodiment. Preferably, the input is made as a combination of entering part of the respective name and a selection from among known patients, treatments or attending persons, or treatment apparatus respectively, in particular on the basis of further criteria such as date of birth, residence, treatment location and/or installation site. This advantageously enables increasing user comfort. The user interface 5 is preferably also provided to allow creating a new patient and/or moreover a new treatment, a new attending person or a new treatment apparatus. Preferably, the patient identifier is determined from these inputs and received for the further procedure in method step S1. Alternatively, the patient identifier can also be entered directly in method step S1 and thus received. Also preferably, the treatment identifier of the treatment to be performed is determined from these inputs in method step S2. Alternatively, the treatment identifier can also be determined by said treatment identifier being input in method step S2. Lastly, preferably the practitioner identifier is determined from these inputs and received for the further procedure in method step S8. Alternatively, the practitioner identifier can also be entered directly in method step S8 and thus received.

Based on the patient identifier from method step S1, one or more patient characteristics are determined by means of an allocation rule for patient characteristics 6 in method step S6. The allocation rule for patient characteristics 6 is thereby constructed to allocate one or more patient characteristics in each case to a patient identifier. Preferably, this allocation rule for patient characteristics 6 is configured as a database. In particular, the allocation rule for patient characteristics 6 can be a table of a relational database such as an SQL database having at least two columns, whereby the respective patient identifiers are stored line-by-line in the one column and the respectively allocated patient characteristics; i.e. particularly identifiers of patient characteristics, line-by-line in the other column; thus, each patient characteristic stored in a line of a table correlates to a patient identifier. In particular, the table can have multiple lines with the same patient identifier and thus have multiple patient characteristics correlated to a patient identifier. This advantageously enables patient characteristics to be efficiently and/or reliability allocated to a patient identifier; i.e. in particular also with lower computing power compared to other solutions and/or based on the proven technology of relational databases. A further advantage can relate to tables in typical relational databases; i.e. in particular the allocation rule for the patient characteristics 6 table, being adaptable and thus in particular being able to create new patients and/or new patient characteristics.

Based on the treatment identifier from method step S2, one or more treatment characteristics are determined by means of an allocation rule for treatment characteristics 7 in method step S7. The remarks made with respect to the allocation rule for patient characteristics 6 thereby apply accordingly to the allocation rule for treatment characteristics 7. Alternatively or additionally, the allocation rule for treatment characteristics 7 can also be designed as static allocation. In particular, each treatment identifier or the portion of the treatment identifiers under static allocation can thereby be correlated to a memory index relating to a data memory, in particular a main memory, whereby a respective treatment characteristic or list of treatment characteristics or list of memory indices on respective treatment characteristics are in each case stored in the data memory with the respective memory index. One advantage of static allocation can be it being particularly efficient and/or allowing quick allocation; i.e. in particular with little computing time, since no relational database needs to be operated and/or the data and/or allocation is already provided, in particular directly, in the main memory. Static allocation can thereby be of particular advantage when the treatments and their characteristics or at least a portion of the treatments and allocated treatment characteristics, for which medical accessories are to be selected in accordance with the method of FIG. 1, are already established upon implementing of the method or can, should and/or need to be changed only together with a revising of the method implementation Based on the practitioner identifier from method step S8, one or more practitioner characteristics 8 are determined by means of an allocation rule for practitioner characteristics 7 in method step S9. The remarks made with respect to the allocation rule for patient characteristics 6 and treatment characteristics 7 thereby apply accordingly to the allocation rule for practitioner characteristics 8.

In method step S3, an accessory database 3 is compared to the actual inventory 4 of stocked medical accessories. The actual inventory 4 can thereby preferably be in a storage area or divided into a plurality of storage areas in which respective medical accessories, in particular medical accessories 1 and 2, are stored and thus represent the respective actual inventory of the respective storage area. The accessory database 3 comprises data sets on at least the two medical accessories 1 and 2. In particular, the accessory database 3 can also comprise data sets on further medical accessories. At least one respective data set on medical accessories 1 and/or 2 identifies in each case one or more characteristics from the accessory characteristics, patient characteristics, treatment characteristics and practitioner characteristics group. Preferably, at least one accessory characteristic corresponds to at least one patient characteristic, treatment characteristic or practitioner characteristic. Preferably, the accessory database 3 is designed as a relational database, in particular an SQL database. Preferably, the medical accessories 1, 2 within the respective storage areas are detected by means of a detection device, in particular in parallel or sequentially, in order to compare the accessory database 3 with the actual inventory 4. Also preferably and alternatively or additionally in the comparing of the accessory database 3 to the actual inventory 4, one or more detection devices detects the medical accessories to comprise the actual inventory 4 as well as the medical accessories to be removed from the actual inventory 4. Such detection devices can in particular be imaging systems designed to capture at least one image of a medical accessory, for instance via a camera, the captured image being allocated in each case to a medical accessory. Such detection devices can also be barcode readers designed to detect a barcode respectively disposed on a medical accessory—for instance a 1D barcode; i.e. a barcode in the narrower sense, or a 2D code—and thereby identify the respective medical accessory. This same applies analogously to RFID readers and medical accessories identified by RFID. Preferably, at least one such detection device is or is to be provided, in particular as a method step of the method of the present preferential embodiment. When comparing S3 the accessory database 3 to the actual inventory 4, the number of similar medical accessories stocked in the actual inventory 4 is preferably stored in each case in at least one data set on the respective medical accessories. This thereby advantageously enables the volume of data on similar medical accessories and/or the computing power needed to determine the number of similar medical accessories in stock to be reduced. In one preferential alternative, one data set each is created on each medical accessory stocked in the actual inventory 4 for just this respective individual medical accessory or, respectively, the data set on the respective medical accessory is deleted if it is no longer in stock. This thereby advantageously enables determining whether each respective medical accessory is in stock and/or storing additional data on the respective medical accessory, for instance the expiration date or the respective storage location.

In method step S4, a medical accessory suited to the patient treatment to be performed is selected from the actual inventory 4 via the accessory database 3 and on the basis of the patient characteristics, treatment characteristics and practitioner characteristics determined in method steps S6, S7 and S9. In particular, the respective characteristics can thereby be stored in the accessory database 3, for instance for logging the treatments and/or the need for or consumption of medical accessories, and/or the respective characteristics sent to the accessory database 3 for retrieval from the accessory database 3. Thus, in particular in the preferential embodiment of the accessory database 3 as a relational database, a database query, in particular an SQL query with the SQL database, can be generated using the respective characteristics.

Lastly, in method step S5, the selected medical accessory is segregated; i.e. preferably identified in the accessory database 3 as segregated, transported to an output location, in particular to a segregating apparatus, provided there for physical output and/or physically output there—i.e. in particular dispensed to an attending person, a treatment apparatus, a transporting person or a transport apparatus. FIG. 1 thereby illustrates the segregating of medical accessory 1, since same was selected in an example procedure of the method in method step S4, whereas medical accessory; i.e.

in particular accessory set 2—indicated by the dashed lines—was not segregated as it was not selected in the example procedure.

The present example procedure type is in particular the selecting of a medical accessory for creating access to a patient's blood circulation, for instance prior to or as part of a patient dialysis treatment. The medical accessory 1 is thereby a cannula and the medical accessory set 2 is a box containing a cannula, a disinfectant wipe and a pair of disposable gloves of a specific size. One accessory characteristic of the cannula 1 is its size, e.g. in gauge. The accessory characteristics of the medical accessory set 2 are at least the medical accessories thereby compiled plus their accessory characteristics, here thus at least the presence of the cannula, the disinfectant wipe and the disposable gloves as well as the cannula size and the size of the disposable gloves as well as preferably the presence of allergens, for instance in the disinfectant wipe.

In this example procedure, the patient identifier of the example patient is received in method step S1 and the patient characteristics of the example patient determined with the allocation rule for patient characteristics 6 in method step S6, whereby such a patient characteristic is an allergy to specific disinfectants. Also determined in method step S2 in this example procedure is the treatment identifier; thus, here the identifier to establish blood circulation access for a dialysis treatment, and the treatment characteristics relative to creating the access to the blood circulation determined in method step S7 with the allocation rule for treatment characteristics 7. Such treatment characteristics are at least the necessary cannula sizes for the dialysis treatment as well as the requirement of having a disinfected area of skin. The practitioner identifier is additionally determined in this example procedure in method step S8; i.e. in the present case, which treatment apparatus is to create the access or, respectively, in the alternative illustrated by the dashed lines, which physician is to create the access, and the practitioner characteristics determined in method step S9 with the allocation rule for practitioner characteristics 8; i.e. in the present case, the properties of the treatment apparatus—particularly whether or not same has its own respective sterilizing device and disinfecting device in this example procedure—or, in the alternative, the hand size of the treating physician.

By comparing S3 to the actual inventory 4, both the cannula 1 as well as accessory set 2 are in stock in this example procedure.

During selection S4, the accessory database 3 is queried as to suitable medical accessories which have no allergens relative to the allergies of the example patient and are of the cannula size needed for the dialysis treatment and which are necessary for a disinfected area of skin in terms of the practitioner identifier as well as in terms of the practitioner characteristics. In the example procedure, cannula 1 is selected based on the sterilizing device and disinfecting device of the treatment apparatus since no additional medical accessory is needed for the area of skin to be disinfected. In the alternative, accessory set 2 is selected, which additionally enables the disinfection of the skin area as well as the at least substantially sterile handling of the cannula using the gloves, whereby the disinfectant wipe has no allergens relevant to the example patient's allergy and the size of the disposable gloves corresponds to the size of the physician's hands—thus, for instance, size L gloves with a physician hand circumference of 24 cm (see e.g. https://www.euromed-gmbh.de/handschuhgroessen-ermitteln as to the correspondence of glove sizes and hand sizes). Lastly, the selected cannula 1 is segregated (or the accessory set 2 respectively in the alternative).

FIG. 2 shows a flow chart to illustrate a further preferential embodiment of the inventive method for selecting a medical accessory 1, 2, 11.

The actual inventory 4 of stocked medical accessories is divided into two storage areas, the storage area 9 and the further storage area 10, and comprises medical accessory 1, accessory set 2 and the further medical accessory 11. Preferably, the two storage areas 9, 10 each have their own storage conditions and, further preferably, the storage conditions can be regulated or at least controlled, in particular separately. The provisioning of the storage areas and/or the control or regulating of the respective storage conditions thereby in particular constitute method steps of the method of the present further preferential embodiment. The method step S10 is performed twice in this embodiment; firstly, the medical accessory 1 as well as the medical accessory set 2 is stored in storage area 9, its storage conditions at least substantially corresponding to the required storage conditions for the medical accessories 1, 2, and secondly, the further medical accessory 11 is then stored in the further storage area 10, its storage conditions at least substantially corresponding to the required storage conditions for the medical accessory 11.

Method step S3 is also performed twice in this embodiment; first, the stocked medical accessories 1, 2 stored in storage area 9 are compared to an accessory database 3 and, second, the available medical accessories stored in the further storage area 10, in particular the further accessory 11, are compared to the accessory database 3. The remarks made with respect to the accessory database and with respect to comparing the accessory database to the actual inventory in FIG. 1 also apply accordingly to the embodiment in FIG. 2.

Method step S11 is also performed twice in this embodiment, namely in each case for the two storage areas 9, 10, whereby the actual storage conditions of the respective storage area 9, 10 are in each case detected. Preferably, same are detected by means of storage condition sensor devices, preferably for instance temperature sensor devices, moisture sensor devices, radiation sensor devices, in particular light sensor devices, and/or sensor devices for chemicals such as acids or caustic solutions. Should the actual storage conditions of a medical accessory differ or have deviated from the required storage conditions according to process condition C1, said medical accessory will be identified as not being in stock, in particular in the respective storage area 9 or the accessory database 3 or both, in method step S12. A medical accessory identified as such, here in particular medical accessory 11, will ultimately be isolated in method step S13 and transported to a segregation area 12 thereto. Preferably, the segregation area 12 is a container for medical accessory disposal. A signal is also preferably output for the disposal of the isolated medical accessory. This thereby advantageously enables medical accessories which failed to adhere to their storage conditions to be isolated and thus excluded from selection for the treatment. One advantage of transporting to a segregation area 12 can be seen in the isolated medical accessories being physically separated from the medical accessories available to be selected for the treatment. Disposal is thereby additionally facilitated. Lastly, the output disposal signal enables disposal to occur as a function of the signal and, in particular, enables the disposal to be automated, whereby in particular personnel workload can be reduced and/or efficiency increased.

A patient identifier of a patient to be treated is received in method step S1 and a treatment identifier of a treatment to be performed is determined in method step S2. This can ensue as per FIG. 1. In a preferential alternative variant, the treatment identifier is determined on the basis of the patient identifier. In particular, a patient identifier can be correlated with one or more treatment identifiers such that the treatment identifier of the treatment to be performed can be determined from this correlation. Preferably, the treatment identifier of the treatment which is to be prioritized on the basis of a predefined criterion for treatment priority is thereby determined as the treatment identifier of the treatment to be performed.

In the embodiment depicted in FIG. 2, the selection of a suitable medical accessory for the treatment of the patient to be performed occurs in method step S4 by means of the accessory database 3 and directly on the basis of the patient identifier and the treatment identifier as well as the actual inventory 4. In particular, patient/treatment characteristics are not initially assigned to the patient identifier/treatment identifier and then a medical accessory selected on the basis thereof. For the direct selection, the accessory database comprises data sets on at least the medical accessories 1, 2, 11, whereby at least one data set on the medical accessory 1, 2 and/or 11 in each case comprises at least one patient identifier and/or treatment identifier. In particular, a specific medical accessory is thus associated with a specific treatment via a treatment identifier or, respectively, associated with a specific patient via a patient identifier. In a preferential alternative variant, the selection can also ensue as described with respect to FIG. 1; i.e. in particular with patient characteristics, treatment characteristics, practitioner characteristics and/or accessory characteristics.

The selected medical accessory, here in particular medical accessory 1, is ultimately segregated in method step S5.

An example procedure for the embodiment of FIG. 2 is in particular the storage and selection of medical accessories for affixing a catheter to a patient, for instance in preparation for or as part of a patient dialysis treatment. The patient identifier and the treatment identifier are, as stated above, received in method step S1, or respectively determined in method step S2; i.e. in particular the treatment identifier for the catheter attachment or for the dialysis treatment determined, which comprises catheter attach-ment as part of the treatment and thus requires the corresponding medical accessories.

The medical accessory 1 is in this example procedure preferably three adhesive strips of a predefined length, for instance 3 cm, 5 cm and 8 cm, supplied together in sterile packaging for affixing a catheter to a patient. The medical accessory set 2 can be configured as described with reference to FIG. 1. The further medical accessory 11 is an adhesive strip roll—for instance of an original length of 3 m, from which in each case a section is separated for the respective treatment, preferably by means of an adhesive strip dispenser. Both the data set on the sterile-packed adhesive strips 1 as well as the data set on the adhesive strip roll 11 exhibit the treatment identifier relative to catheter attachment.

The storage conditions for the sterile-packed adhesive strips 1 and for accessory set 2 correspond to a normal atmospheric environment; i.e. approximately 25° C. with humidity between 10% and 90%. Therefore, in method step S10, they are stored in storage area 9 which does not have any special provisions for climate control. In contrast, adhesive strip roll 11 is not in sterile packaging such that one of the necessary storage conditions is in particular lower humidity, preferably below 20% humidity, in particular in order to prevent bacterial contamination. To that end, the further storage area 10 is climate-controlled and thus at least the humidity controlled or regulated. The adhesive strip roll 11 is stored in the air-conditioned further storage area 10 in method step S10. The respective actual storage conditions are determined in method step S11. While there is no deviating of the actual storage conditions in storage area 9, excessive humidity develops in the case of storage area 10 in the example procedure outlined here, for instance a humidity of 50% over the span of 1 hour. As a result, the adhesive strip roll is identified as not being in stock in method step S12 and transported to a segregation area 12 in method step S13. As indicated by the dashed lines in FIG. 2, method step S12 is not performed for storage area 9, or respectively for the medical accessories 1, 2 stored therein, since process condition C1; i.e. the actual storage conditions deviating from the required storage conditions, does not occur.

Thus, the sterile-packed adhesive strips 1 as well as the medical accessory set 2 are available for selection in method step S4 but not, however, the adhesive strip roll 11. Therefore, the sterile-packed adhesive strips 1, the data set of which comprises the treatment identifier, is selected as the suitable medical accessory while the adhesive strip roll 11, since it is identified as not in stock, is not selected, even though the adhesive strip roll data set also comprises the treatment identifier.

Yet a further embodiment of the inventive method for selecting a medical accessory is illustrated in FIG. 3 by means of a flow chart. The method begins at process start SA and ends at process end SΩ. A patient identifier is received in method step S1; a treatment identifier is determined in method step S2; an accessory database is compared to the actual inventory of stocked medical accessories in method step S3. Preferably, these method steps are designed in accordance with the embodiment of FIG. 1 or FIG. 2 or a combination thereof.

The assembling of a medical accessory set in method step S14 takes the place of selecting individual medical accessories in method step S4, whereby method step S4 is performed at least once thereto as a sub-step of method step S14. After method step S4 has been performed, a check is made pursuant to process condition C3 as to whether all the medical accessories necessary for the treatment have been selected. Should this not be the case, method step S4 is iteratively performed and process condition C3 rechecked until all the medical accessories necessary for the treatment have been selected. A subsequent check pursuant to process condition C2 is then made as to whether one, preferably at least two, or further preferentially all of the medical accessories of a medical accessory set compiled in a predefined manner have been selected for the treatment. In this case, this predetermined accessory set is selected in method step S15 instead of the individual medical accessories which the accessory set comprises. In particular, further selected medical accessories not comprised by the predetermined accessory set can thereby be further selected for the treatment or for the accessory set assembled on the basis of the selection respectively. Lastly, the selected medical accessories and/or the predetermined accessory set are assembled into the accessory set compiled on the basis of the selection. Preferably, the selected medical accessories and/or the predetermined accessory set is/are thereby accommodated in a container, in particular an accessory box. The selection-based accessory set assembled can thereby in particular also comprise at least one predetermined accessory set—thus in particular a predefined assemblage of some of the selected medical accessories.

Lastly, the accessory set assembled on the basis of the selection is segregated in method step S5.

FIG. 4 schematically depicts an embodiment of the inventive sorting apparatus 20 for a medical accessory 1, 2, 11, same being configured to segregate a medical accessory 1, 2, 11—thus, in particular also an accessory set 2. It comprises a supply storage 22 and a dispenser device 23. The supply storage 22 is designed to initially receive the suitable medical accessory or accessories 1, 2, 11 for the patient treatment to be performed upon segregation or selection respectively, thereby prepare same for the actual dispensing, and subsequently, in particular when a delivery criterion exists, release the respective medical accessories to be dispensed, in particular illustrated here by medical accessory 1, to the dispenser device 23; i.e. in particular dispose same on the dispenser device 23. The dispenser device 23 is preferably designed, as illustrated, similar to a drawer. Alternatively and also preferentially, the dispenser device 23 can in particular be designed as a discharge chute. The dispenser device 23 is configured to release the respective medical accessory 1, 2, 11 to be dispensed (illustrated here by medical accessory 1), preferably upon said dispenser device 23 being actuated—in particular, the drawer-like dispenser device 23 being opened.

According to the preferential variant depicted in FIG. 4, the segregating apparatus 20 further comprises an identification device 21. The identification device 21 is designed to identify an attending person, a treatment apparatus, a transporting person or transport apparatus for medical accessories and/or accessory sets associated with the attending person and determine an associated practitioner identifier, in particular a practitioner identifier pursuant to the example embodiment of FIG. 1. To that end, the identification device preferably comprises a camera, a user interface—in particular for user name or password input—, a barcode reader, RFID reader and/or a near-field communication device (in the sense of a NFC system), whereby one or more identifying characteristics can be detected, as well as an allocation rule for identifying characteristics which allocates at least one and preferably at least three identifying characteristics to at least one practitioner identifier. This practitioner identifier can in particular be a dispensing criterion specifying which medical accessories 1, 2, 11 stored in the supply storage 22 are to be dispensed; i.e. in particular disposed on the dispenser device 23. The dispenser device 23 is configured to only release the respective medical accessory to be dispensed when the practitioner identifier determined by means of the identification device 21 corresponds to the practitioner identifier from the medical accessory selection. This thereby advantageously enables ensuring the providing of the respective medical accessory to the attending person or the treatment apparatus in each case. Particularly able to be prevented is a medical accessory reaching the wrong attending person or treatment apparatus, and thus the wrong patient, whereby efficiency, treatment quality and/or treatment safety can be increased. At the same time able to be advantageously prevented is the removal, tampering with or contaminating of medical accessories, for instance surgical instruments, narcotics or dressing materials, by unauthorized persons.

FIG. 5 schematically depicts an embodiment of the inventive selection apparatus 30 for medical accessories 1, 2, 11. Same is designed to realize a method in accordance with the first aspect of the invention, in particular a method pursuant to the embodiment of FIG. 1, FIG. 2, FIG. 3 or a combination thereof and thereby receive at least one patient identifier, determined a treatment identifier, compare an accessory database 3 to an actual inventory of medical accessories, select a suitable medical accessory 1, 2, 11—thus in particular also an accessory set 2—for the patient treatment to be performed as well as segregate the selected medical accessory. The selection apparatus 30 comprises a storage area 9, a further storage area 10, a segregation area 12, two segregating apparatus 20, a data processing device 31 with a user interface 5, a microprocessor 32, a main memory 33 and a non-volatile data storage 34, whereby the accessory database 3 of the selection apparatus 30 is installed on the data processing device 31, a gripping device 35 and a detection device 36. Preferably, the selection apparatus 30 additionally comprises a storage area for accessory boxes 38 in which are arranged one or more accessory boxes 37 provided to accommodate one or more selected medical accessories and in particular form an accessory set with same.

The actual inventory is, particularly as is described relative to FIG. 2, divided among a plurality of storage areas, particularly storage area 9 and further storage area 10, whereby at least medical accessory 1 and accessory set 2 are disposed in storage area 9 and further medical accessory 11 disposed in further storage area 10. Preferably, storage area 9 is designed as a racking system and further storage area 10 as a freezer or climate-controlled cabinet. Preferably, the segregation area 12 is designed as a disposal container accommodating medical accessories to be segregated and in particular discarded.

At least one of the segregating apparatus 20 is preferably designed as is described with respect to FIG. 4. The selection apparatus 30 can also comprise only one segregating apparatus or also more than two segregating apparatus.

The user interface 5 is preferably designed as a touch-sensitive screen. Preferably, the user interface 5 is arranged on one of the segregating apparatus 20 or on the data processing device 31. The selection apparatus 30 can also have further user interfaces. These can in particular be further touch-sensitive screens or independent terminals for user input/output, preferably personal computers, tablets or computers in an ambulance which communicate with the data processing device 31 by means of one or more communication interfaces of the user interface or the data processing device 31 respectively. In particular, a patient identifier, treatment identifier and/or practitioner identifier can be determined or received respectively by means of the user interface 5. Alternatively or additionally, at least one user interface can also be configured as a barcode reader or RFID reader designed to read or respectively receive a patient identifier, treatment identifier and/or practitioner identifier.

The gripper device 35 is designed to grasp a selected medical accessory, for instance medical accessory 1, and transport same upon segregation to one of the segregating apparatus 20, upon assembly of an accessory set to one of the accessory boxes 37, and/or upon isolation to segregation area 12. The detection device 36 is designed to detect the medical accessories in stock. Preferably, the detection device 36 is designed as a barcode reader and arranged on the gripper device 35 such that it, together with a part of the gripper device, can be moved toward individual medical accessories and thus be able to detect the barcode of the respective medical accessory. One advantage of this arrangement of the detection device 36 can be in the detection device 36 being able to detect the respective medical accessory both for the accessory database 3 comparison as well as during or respectively prior to grasping and, in particular, the detection device 36 not needing to be designed to detect a plurality or all of the medical accessories at the same time. In particular, the available medical accessories 1, 2, 11 can thus be detected sequentially/one after the one and the accessory database 3 thus compared and/or a selected medical accessory detected prior to the segregating, isolating or assembling into an accessory set and thus reduce the risk of the gripper device 35 grabbing an incorrect medical accessory.

FIG. 6 shows a schematic representation of an embodiment of the inventive system 40 for medical accessories. Same comprises a stationary selection apparatus 41, a mobile selection apparatus 42, a treatment apparatus 43 and a transport apparatus 44. Preferably, the stationary selection apparatus 41 is designed as per the embodiment of FIG. 5, whereby it can hold—particularly because it is stationary—a plurality of medical accessory stock and/or store medical accessories at the storage conditions respectively adapted thereto. The mobile selection apparatus 42 is preferably of similar design to the FIG. 5 embodiment, whereby the physical dimensions and/or weight including the medical accessories is less than with a stationary selection apparatus and the mobile selection apparatus 42 preferably has rollers or belts in order to facilitate the transporting of the mobile selection apparatus 42. Such a mobile selection apparatus can also comprise only one storage area and/or at least two or more segregating apparatus respectively configured as storage areas for a portion of the medical accessories.

The treatment apparatus 43 is disposed at a first treatment location 45. The transport apparatus 44 is thereby designed to transport medical accessories from one of the selection apparatus, in particular the stationary selection apparatus 41, to the first treatment location 45, and preferably to the treatment apparatus 43, as well as preferably equip the treatment apparatus 43 with the medical accessories for the treatment apparatus transported there. This advantageously enables the particularly automatic transport of the respective medical accessories needed for the treatment to be performed to the treatment apparatus 43, whereby in particular efficiency can be increased and/or personnel workload reduced. One advantage of a stationary selection apparatus 41 and transport apparatus 44 combination can also lie in the medical accessories necessary for the respective treatment being able to be flexibly transported to different treatment locations and/or other, unneeded medical accessories not having to be unnecessarily transported.

The mobile selection apparatus 42 is disposed at a second treatment location 46. One advantage of the mobile selection apparatus 42 can be in the respective medical accessory needed for the treatment being provided for the respective treatment, provided it is stocked in said mobile selection apparatus, at the treatment location, or respectively the location of the mobile selection apparatus, without a prior medical accessory selection and subsequent transport.

With this system for medical accessories, medical accessories can be provided at different treatment locations, for instance first treatment location 45 and second treatment location 46, whereby patients can in particular be cared for at different treatment locations, thereby enabling flexible managing and thus efficient use of available treatment locations, and/or a respective patient who has changing medical accessory needs can also remain at one treatment location, thereby enabling increased patient comfort and/or increased treatment quality.

While the preceding describes at least one preferential embodiment, it will be noted that there is a great number of variations thereof. It is also to be noted that the embodiments described only represent non-limiting examples and are not thereby intended to limit the scope, the applicability or the configuration of the apparatus and methods described herein. Rather, the foregoing description will provide a person skilled in the art with guidance for implementing at least one embodiment, wherein it is to be understood that a variety of changes can be made to the functioning and arrangement of the elements described in a preferential embodiment without thereby departing from the subject matter respectively set forth in the accompanying claims nor from legal equivalents thereof.

LIST OF REFERENCE NUMERALS 1 medical accessory
2 medical accessory set
3 accessory database
4 actual inventory of stocked medical accessories
5 user interface
6 allocation rule for patient characteristics
7 allocation rule for treatment characteristics
8 allocation rule for practitioner characteristics
9 storage area
10 further storage area
11 further medical accessory
12 segregation area
20 segregating apparatus
21 identification device
22 supply storage
23 dispenser device
30 selection apparatus
31 data processing apparatus
32 microprocessor
33 main memory
34 non-volatile memory
35 gripper device
36 detection device, particularly designed as a barcode reader
37 accessory box
38 storage area for accessory boxes
40 medical accessory system
41 stationary selection apparatus
42 mobile selection apparatus
43 treatment apparatus
44 transport apparatus
45 first treatment location
46 second treatment location
SA process start
SΩ process end
S1 method step: receive patient identifier
S2 method step: determine a treatment identifier for treatment to be performed
S3 method step: accessory database comparison
S4 method step: select suitable medical accessory for the patient treatment to be performed
S5 method step: segregate the selected medical accessory
S6 method step: determine patient characteristics
S7 method step: determine treatment characteristics
S8 method step: receive practitioner identifier
S9 method step: determine practitioner characteristics
S10 method step: store medical accessory
S11 method step: detect actual storage conditions
S12 method step: identify a medical accessory as not in stock
S13 method step: isolate a medical accessory
S14 method step: assemble a medical accessory set
S15 method step: select a medical accessory set instead of individual medical accessories C1 process condition: actual medical accessory storage conditions differ from the required storage conditions C2 process condition: one, at least two, or all medical accessories of the medical accessory set are selected for the treatment C3 process condition: all medical accessories needed for the treatment have been selected

The invention claimed is:

1. A method for selecting a medical accessory for a treatment of a patient, wherein the method comprises the following method steps:
receiving a patient identifier which identifies the patient to be treated;
determining a treatment identifier for the treatment to be performed, which identifies the patient treatment to be performed;
determining patient characteristics by means of the patient identifier and based on an allocation rule for patient characteristics, which is constructed to allocate one or more patient characteristics to a respective patient identifier;
determining treatment characteristics by means of the treatment identifier and based on an allocation rule for treatment characteristics which allocates one or more predetermined treatment characteristics of the respective treatment in each case to at least two treatments;
comparing an accessory database containing data sets on at least two medical accessories for one or more patient treatments to an actual inventory of stocked medical accessories in a supply storage, the actual inventory being detected by a detection device, wherein at least two data sets of the accessory database in each case identify one or more characteristics from the group of accessory characteristics, patient characteristics, and treatment characteristics;
identifying a medical accessory in order to select a suitable medical accessory by means of the accessory database, its associated data set exhibiting accessory characteristics, patient characteristics, and treatment characteristics corresponding to the specific patient characteristics determined on the basis of the patient identifier and the specific treatment characteristics determined on the basis of the treatment identifier respectively, the suitable medical accessory further selected on the basis of the actual inventory detected by the detection device; and
dispensing the selected medical accessory, from the supply storage, with a dispenser device, to an attending person or a treatment apparatus, or to a transporting person or transport apparatus associated with said attending person or treatment apparatus, the selected medical accessory being configured to be used for the treatment of the patient.

2. The method according to claim 1, further comprising:
receiving patient characteristics of the patient from a patient examining device or a data network for patient characteristics; and
storing the received patient characteristics in a patient characteristic memory, by means of which the allocation rule for patient characteristics allocates one or more patient characteristics in each case to a patient identifier.

3. The method according to claim 1, further comprising:
determining one or more patient treatments to be performed on the basis of the patient characteristics; and
outputting the treatments to be performed to a user interface.

4. The method according to claim 3, further comprising the following method step to determine the treatment identifier of the treatment to be performed:
selecting a treatment as the first to be performed from among the patient treatments to be performed on the basis of a predefined criterion for treatment priority; and
specifying the treatment identifier of said treatment to be performed first as the treatment identifier of the treatment to be performed.

5. The method according to claim 1, wherein, to determine the treatment identifier of the treatment to be performed, an input of the treatment to be performed is received at a user interface and said input is allocated to the respective treatment identifier.

6. The method according to claim 1, wherein to select the suitable medical accessory, a first suitable accessory is determined by means of the accessory database, and, if same is not stocked in the actual inventory, ascertaining an alternative suitable accessory until determining said respective alternative suitable accessory is in stock or until it is determined that none of the suitable accessory alternatives are in stock.

7. The method according to claim 1, wherein, should no suitable medical accessory be in stock in the actual inventory during the selection of the suitable accessory, a signal on accessory shortage is output which identifies the not-in-stock state of the suitable accessory or accessories.

8. The method according to claim 1, wherein the at least two data sets of the accessory database in each case identify the expiration date of the medical accessory associated with the respective data set; and wherein the method further comprises one or more of the following method steps:
identifying a medical accessory as not in stock when it is past its expiration date;
isolating a medical accessory past its expiration date; and/or
outputting a signal for the disposal of medical accessories which identifies the medical accessory past its expiration date to be isolated and/or discarded.

9. The method according to claim 1, wherein the at least two data sets of the accessory database identify in each case the required storage conditions of the medical accessory associated with the respective data set; and wherein the method further comprises one or more of the following method steps:
providing at least two storage areas, each with their own respective storage conditions and their storage conditions able to be separately controlled or regulated;
storing in each case the portion of the medical accessories in one of at least two storage areas with storage conditions at least substantially corresponding to the required storage conditions of the respective medical accessories;
detecting the actual storage conditions prevailing for the actual inventory of stocked medical accessories;
identifying a medical accessory as not in stock when the actual storage conditions of the medical accessory deviate from the required storage conditions according to a criterion related to the spoilage of the medical accessory;
isolating a medical accessory with actual storage conditions deviating from the required storage conditions according to a criterion related to the spoilage of the medical accessory; and
outputting a signal for the disposal of medical accessories which identifies the medical accessory with actual storage conditions deviating from the required storage conditions which is to be isolated and/or discarded.

10. The method according to claim 1, wherein:
at least two medical accessories are assembled into a medical accessory set in predetermined manner;
the accessory database comprises at least one data set on the medical accessory set and/or the data sets on the at least two medical accessories of the accessory set also identifies the medical accessory set in addition to the respective medical accessories;
the accessory database is compared to the actual inventory of stocked medical accessory sets; and
the medical accessory set is selected for the patient treatment to be performed when one, at least two, or all of the medical accessories of the medical accessory set are selected for the treatment, and the medical accessory set is dispensed instead of individual medical accessories.

11. The method according to claim 1, further comprising:
assembling a medical accessory set for the patient treatment to be performed based on the selection of one or more suitable medical accessories for the patient treatment to be performed; and
dispensing the assembled medical accessory set instead of individual medical accessories suitable for the treatment and/or instead of at least some of the medical accessories suitable or respectively necessary for the treatment.

12. The method according to claim 1, further comprising:
receiving a practitioner identifier which identifies an attending person or a treatment apparatus for the patient treatment to be performed; and
determining practitioner characteristics on the basis of the practitioner identifier and by means of an allocation rule for practitioner characteristics, which is configured to allocate one or more practitioner characteristics in each case to a practitioner identifier;
and wherein:
the at least two data sets of the accessory database identify in each case at least one of the practitioner characteristics and/or at least one of the accessory characteristics corresponding to at least one of the practitioner characteristics; and
determining a medical accessory or accessory set in order to select the suitable medical accessory by way of the accessory database, the associated data set of which comprises practitioner characteristics or accessory characteristics corresponding to the practitioner characteristics determined on the basis of the practitioner identifier.

13. A segregating apparatus for medical accessories configured to segregate medical accessories or accessory sets selected in accordance with claim 12, and wherein the segregating apparatus:
comprises an identification device configured to identify said attending person or treatment apparatus, or said transporting person or transport apparatus associated with said attending person or treatment apparatus, and to determine an associated practitioner identifier; and
is further configured to only segregate the medical accessory or accessory set when the practitioner identifier determined by the identification device corresponds to the practitioner identifier in the selection of the medical accessory.

14. A selection apparatus for a medical accessory or accessory set, comprising:
at least one storage area;
a detection device configured to detect an actual inventory in the at least one storage area;
a data processing device comprising a user interface, a microprocessor, a memory, and an accessory database, wherein a computer program is installed on the data processing device and the selection apparatus is configured by the computer program to: (1) identify a patient to be treated upon receiving a patient identifier; (2) determine a treatment identifier for the treatment to be performed, which identifies the patient treatment to be performed; (3) determine patient characteristics by means of the patient identifier and based on an allocation rule for patient characteristics, which is constructed to allocate one or more patient characteristics to a respective patient identifier; (4) determine treatment characteristics by means of the treatment identifier and based on an allocation rule for treatment characteristics, which allocates one or more predetermined treatment characteristics of the respective treatment in each case to at least two treatments; (5) compare the accessory database containing data sets on at least two medical accessories for one or more patient treatments to the actual inventory of stocked medical accessories in the at least one storage area, wherein at least two data sets of the accessory database in each case identify one or more characteristics from the group of accessory characteristics, patient characteristics, and treatment characteristics; and (6) identify a medical accessory in order to select a suitable medical accessory by means of the accessory database, its associated data set exhibiting accessory characteristics, patient characteristics, and/or treatment characteristics corresponding to the specific patient characteristics determined on the basis of the patient identifier or the specific treatment characteristics determined on the basis of the treatment identifier respectively, the suitable medical accessory further selected on the basis of the actual inventory;
a selection device; and
at least one segregating apparatus, wherein the selection device is configured to transport the suitable medical accessory from the at least one storage area to the at least one segregating apparatus.

15. The selection apparatus of claim 14, wherein the selection device is a gripper device, and the detection device is arranged on the gripper device.

16. The selection apparatus of claim 14, wherein the accessory database is installed on the memory.

* * * * *